United States Patent [19]

Schilk

[11] Patent Number: 4,659,584

[45] Date of Patent: Apr. 21, 1987

[54] EYE ROD, PROCESS AND APPARATUS FOR LOADING THE SAME WITH SOLUTIONS OR SUSPENSIONS OF ACTIVE SUBSTANCE

[75] Inventor: Leonhard Schilk, Biberach, Fed. Rep. of Germany

[73] Assignee: Dr. Karl Thomae GmbH, Biberach an der Riss, Fed. Rep. of Germany

[21] Appl. No.: 851,009

[22] Filed: Apr. 11, 1986

[30] Foreign Application Priority Data

Apr. 13, 1985 [DE] Fed. Rep. of Germany ....... 3513288

[51] Int. Cl.⁴ ............ A61K 9/22; A61M 35/00; A01N 1/02; B05C 11/00
[52] U.S. Cl. .................................. 427/2; 118/669; 118/679; 118/691; 604/289; 604/893
[58] Field of Search ............ 118/669, 671, 672, 674, 118/679, 691; 427/2; 604/289, 893

[56] References Cited

U.S. PATENT DOCUMENTS 3,192,796 7/1965 Peeps et al. ............ 118/679 X
3,630,200 12/1971 Higuchi ............... 604/893
3,948,265 4/1976 Ani et al. ............. 128/267

FOREIGN PATENT DOCUMENTS 1541271 4/1971 Fed. Rep. of Germany ...... 604/289
2441191 3/1975 Fed. Rep. of Germany .
2529789 1/1984 France .
2097680 11/1982 United Kingdom .

Primary Examiner—Michael R. Lusignan
Attorney, Agent, or Firm—David E. Frankhouser; Alan R. Stempel

[57] ABSTRACT

The specification describes a process and apparatus for charging eye rods with solutions or suspensions of active substance. The latter are applied dropwise, by means of a micrometering device, to specific points on the eye rods which are set in rotation, and simultaneously or subsequently the solvent or suspension agent is removed.

11 Claims, 6 Drawing Figures

EYE ROD, PROCESS AND APPARATUS FOR LOADING THE SAME WITH SOLUTIONS OR SUSPENSIONS OF ACTIVE SUBSTANCE

The invention relates to eye rods which have a coating of active substance with a defined content of active substance surrounding their outer ends and a process and apparatus for loading these eye rods with solutions or suspensions of active substance. The eye rods are carriers of active substance for application to the eye. The quantity of active substance which is preferably applied to the outer end of a rod can be inserted in virtually quantitative amounts into the conjunctival sac of the lower eyelid by inserting the rod between the eye and the lower lid and rotating it about its axis.

From German Pat. No. 2 441 191, eye rods are known which are characterised in that an active substance intended for the eye is placed on the surface of the end or ends of the carrier in a very thin, uniform, dry and liquid-soluble coating in the quantity corresponding to a single dose for the specific use envisaged. Hitherto, the active substance has been loaded onto the carrier by controlled dipping of the ends of the carriers into a solution of the active substance or by spraying the substance onto the carrier or by applying a dried active substance to the carrier with the aid of an adhesive. In practice, it has been found that the loading of the active substance using the methods described above had the following disadvantages: the dosage metering was too inaccurate; the quantity of active substance in relation to the surface area fluctuated considerably; in the case of spraying, droplets of different diameter were formed, partial vaporisation of the material occurred resulting in uneven coating of the intended zones, while other zones of the carrier which were not supposed to be coated were also given a film of active substance. Spraying the dried active substance onto the rods in the presence of an adhesive also resulted in considerable variations in the quantity of active substance along the zones of the carrier intended to be coated.

It has now been found that these disadvantages can be avoided if solutions or suspensions of active substance in the form of droplets of uniform volume are applied, by means of a micrometering device which always releases the same number of droplets to each carrier, to the zones of a rotating carrier intended for this purpose. The rotation of the carrier ensures a uniform distribution of the solutions or suspensions of the active substance on the zones intended for this. Simultaneous or subsequent evaporation of the solvent or suspension agent and drying of the active substance remaining as a residue by suitable methods of evaporation or drying causes the active substance to adhere to the carrier.

With this method of loading the carrier with active substances the following advantages are achieved: in accordance with the accuracry of the micrometering system, a high accuracy of metering can be achieved; the active substance is uniformly distributed over the zones of the carrier intended to be coated; since the solution or suspension of active substance can be kept in a sealed system the risk of contamination is greatly reduced; evaporation of the solvent and hence a shift in the concentration of active substance in the solvent is prevented; the supply of active substance can be used up entirely without leaving any appreciable residues; multiple coatings can be effected, thus making it possible to produce combined preparations.

The loading of specific zones of the rod-shaped carrier is effected using a combined rotation and transport system which forms a further object of the present invention. An elongate rotation and transporting system is suitable for this purpose but it is also possible to use a round rotation and transporting system consisting of a so-called transporting wheel in conjunction with a rotating belt. Both systems will be described hereinafter, although both operate on the same principle: charging the rods by micrometering, uniform distribution of the active substance round the rods and drying by rotating the rods in a current of hot air or by other suitable drying methods, e.g. with IR radiation or high frequency dryers.

A.

ELONGATE ROTATION AND TRANSPORTING SYSTEM

Brief Description of the Drawings

FIG. I—first embodiment of the method of operation.

FIG. II—second embodiment of the method of operation.

FIG. III—third embodiment of the method of operation.

FIG. IV—horizontal model of apparatus for charging with active substance.

FIG. V—circular model of apparatus for charging the active substance.

FIG. VI—preferred embodiment of an eye rod in cross section.

Description of the Method of Operation with Reference to FIGS. I to III

If a plurality of rods (8) arranged parallel to one another are placed on a flat substrate and the latter is pressed against the underside of a driven conveyor belt (1) the rods are transported in the direction of the end of the belt driving them (see FIG. I). If, instead of being a stationary surface, the substrate is the top of a second conveyor belt (2) which is driven separately in the same direction of rotation at the same speed, the rods are made to rotate without being conveyed (see FIG. II).

Figure 1:
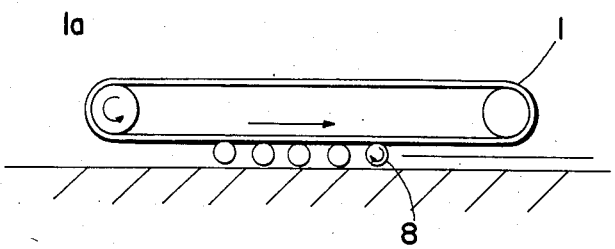
Figure 2:
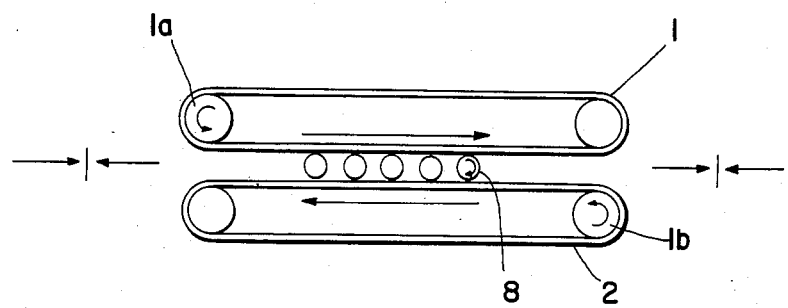
Figure 3:
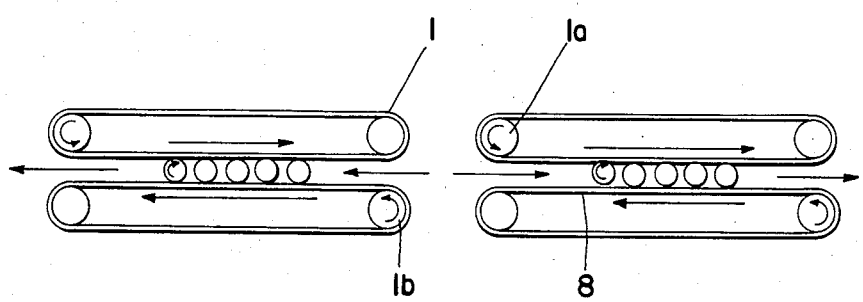
Figure 4:
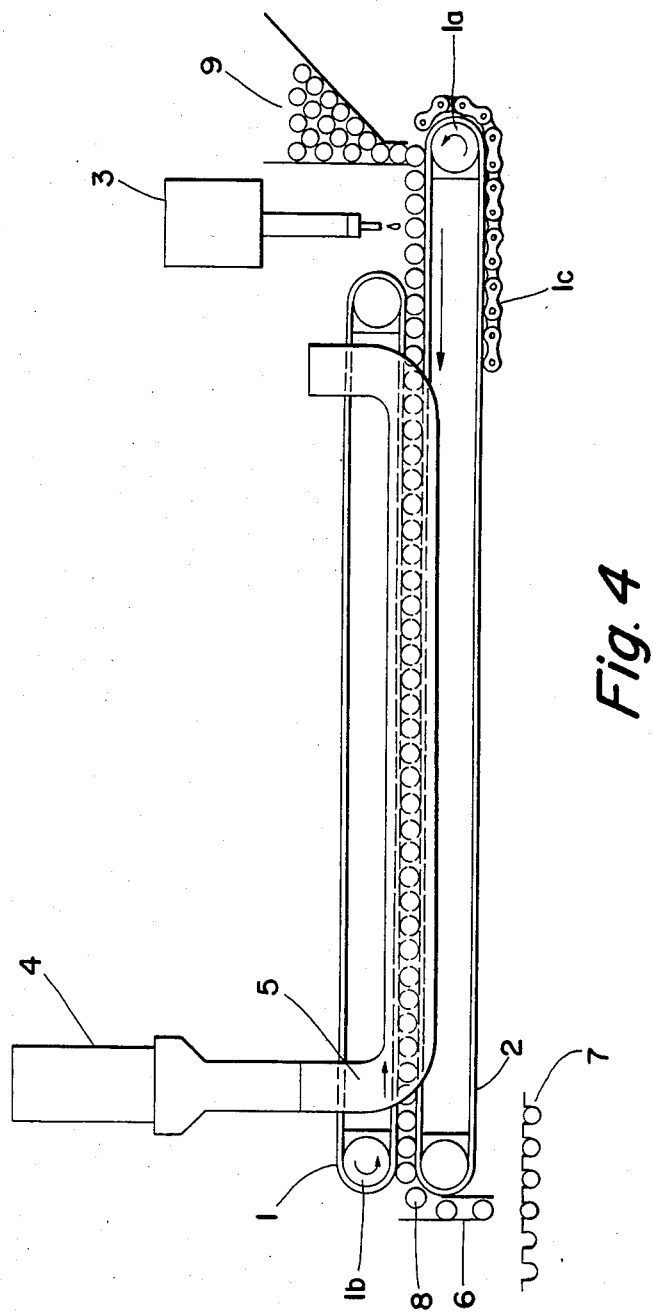
Figure 5:
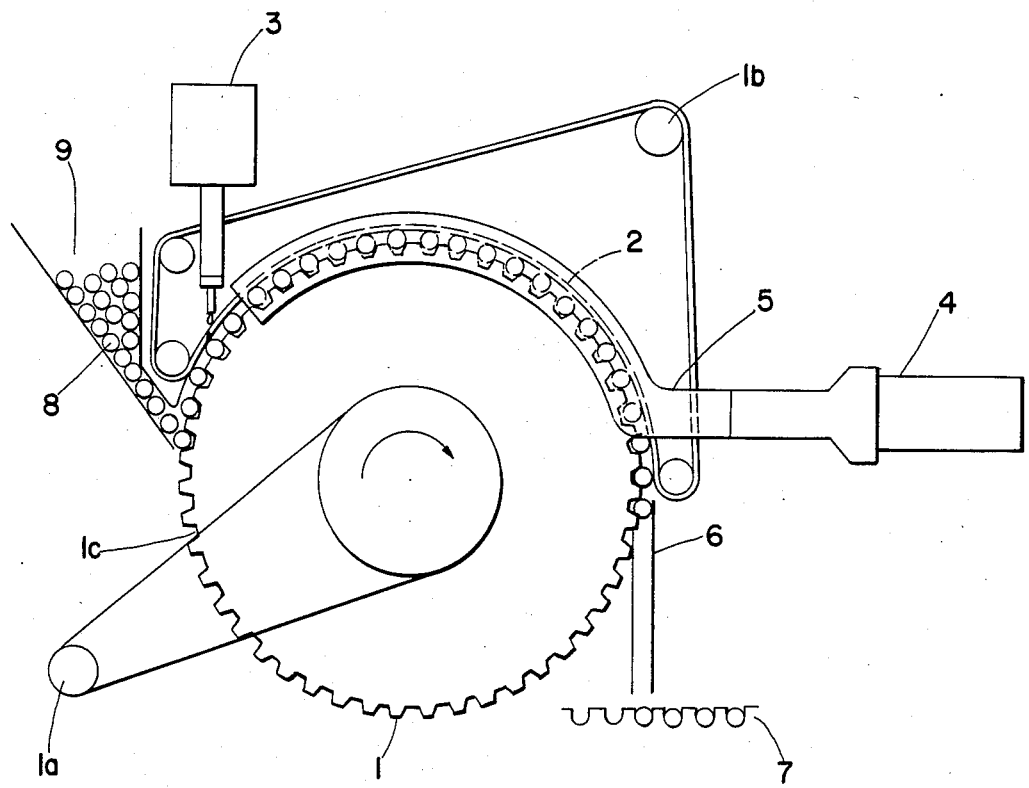
Figure 6:
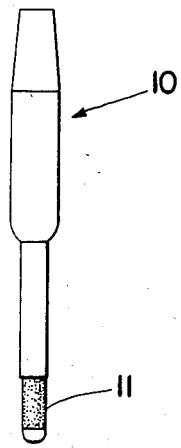

If the two drive motors are operated at different speeds, in addition to the rotary movement there is a conveying movement, the direction of which is determined by the belt travelling faster (see FIG. 3).

In FIGS. I to III, (1) is a conveyor belt, (2) is the conveyor belt running in the opposite direction, (1a) is the drive of conveyor belt (1), (1b) is the drive of conveyor belt (2) and (8) designates the rods which are the carriers of the active substance.

Structure of the Apparatus

The structure of the apparatus is illustrated by way of example of FIG. IV. Two horizontal conveyor belts (1) and (2) are arranged one above the other. Each belt is driven by a separately regulatable motor (1a, 1b). An endless roller chain (1c) is placed around the lower belt in order to guide the rods in parallel manner. The space between two transverse links of the chain serves to receive a rod and is adapted to the shape of the eye rods. The transverse chain links simultaneously serve to take the rods out of the storage area (9). The rollers in the chain are, like the rods, driven by the speed differential of the two belts. The conveyor belts are narrower than the guide chain with the result that the latter is covered only partially, namely in the region of a preferably cylindrical rod handle. The part of the chain which surrounds the tips of the rods is freely accessible for charging the active substance and drying.

The rods carried along by the chain are charged at the metering device (3) with a solution of active substance by dotting a specific number of droplets of the solution onto the tip of the rod after the tripping of a sensor, e.g. by photoelectric means. The uniform distribution of the charging solution around the rods is ensured by rotating the rods (8).

The drying blower (4) supplies hot air to the drying tunnel (5). This drying tunnel consists of a laterally slotted tube. This is fitted over the freely accessible part of the guide chain in such a way that the charged rod tips guided by the chain pass through the drying tunnel.

The hot air current and the continuous rotation of the rods bring about uniform evaporation of the solvent and consequently a homogeneous distribution of the dry active substance around the rod tip.

After leaving the drying tunnel the finished charged rods are transferred from the delivery station (6) to the packaging section (7). Here they are sealed into blister packs, for example.

B.
CIRCULAR ROTATION AND TRANSPORTING SYSTEM

The operating principle of this circular rotation and transporting system is substantially identical to the horizontal arrangement described hereinbefore: charging of the rods by micrometering and uniform distribution of the active substance and drying by rotation of the rods.

The structure differs from the horizontal model in the system for transporting and rotating the rods and is illustrated by way of example in FIG. V. In FIG. V, (1) is a conveyor wheel with a drive (1a) for transporting the rods (8), (2) is a conveyor belt with a drive (1b) which causes the rods to rotate. The conveyor wheel (1) has notches (1c) on its outside, adapted to the outer shape of the eye rods (8). Reference numeral (3) constitutes a metering device for the solution or suspension of active substance. (4) is a drying blower for evaporating the solvent and is connected to the drying tunnel (5). Reference numeral (6) indicates the exit and the delivery of the rods (8) charged with active substance to the packaging station (7).

A large conveyor wheel (1) is set slowly rotating by a drive motor (1a). Against this wheel, a conveyor belt (2) driven by a separate motor (1b) is pressed between the input station (9) and the exit (6). Notches (1c) are formed on the outside of the conveyor wheel. These notches serve to receive the eye rods and hold them in parallel position. The conveyor belt continuously rotates the rods in the notches.

The charging with active substance, drying, delivery and packaging are identical to those described in the elongate rotation and transporting system mentioned hereinbefore.

FIG. VI shows a preferred embodiment of an eye rod in cross section. Reference numeral (10) indicates a handle and (11) designates the zone charged with the active substance.

Suitable metering devices are mechanically, electrically or electronically controlled pump metering systems fitted with suitable nozzles which allow the delivery of a number of drops which remains constant per unit of time, while the size or volume of the drops remains always constant. Piezoelectric oscillators on or in a capillary with a nozzle-shaped exit end have proved suitable; these oscillators are known in principle from ink jet technology. However, it is also possible to use, for example, induction-controlled miniature valves in conjunction with suitably shaped nozzles.

What is claimed is:

1. A process for loading eye rods with a solution or suspension of active substance, said process comprising the steps of applying said solution or suspension of active substance, in the form of droplets of constant volume, with the aid of a micrometering device which always releases the same number of droplets to each eye rod, onto the intended zones of each of said eye rods, rotating each of said eye rods in order to distribute said solution or suspension over said zone and removing the solvent or suspension agent by evaporation, so as to leave the dried active substance on each of said eye rods.

2. An apparatus for loading eye rods with a solution or suspension of active substance, said apparatus comprising a micrometering system for applying droplets of said solution or suspension to each of said eye rods; a drying apparatus for evaporating the solvent or suspension agent from said solution or suspension applied to said eye rods; a first straight or curved belt, driven in a first direction, for conveying said eye rods past said micrometering system and said drying apparatus; and a second, counter rotating, straight or curved belt, which works in conjunction with said first belt in order to cause the rotation of eye rods being conveyed by said first belt.

3. The apparatus of claim 2, further characterized in that said first and second belts are horizontal conveyor belts arranged one above the other in spaced-apart, parallel relationship; and wherein said apparatus further comprises an endless roller chain which is caused by the relative motions of said first and second belts to move in the direction of said first belt, said roller chain having spaces between transverse links thereof which are adapted to receive eye rods and said roller chain serving to retain said eye rods in a spaced-apart, parallel relationship as they are conveyed; a drying tunnel, arranged along said belts, through which said eye rods are conveyed and through which hot air from a drying blower is passed in order to evaporate solvent or suspension agent from said eye rods; a storage area from which eye rods are delivered to said first belt; and a delivery station at which eye rods are removed from said first belt.

4. The apparatus of claim 3, further characterized in that said first and second conveyor belts are narrower than said roller chain and said drying tunnel is fitted over a freely accessible part of the roller chain in such a way that tips of eye rods charged with solution or suspension pass through said drying tunnel.

5. The apparatus of claim 2 wherein said first belt is a conveyor wheel driven in a first direction and having notches or recesses for receiving eye rods on the outside surface thereof, said second belt being positioned so as to abut said conveyor wheel between an input point and an exit point, and wherein said drying apparatus comprises a drying blower connected to a drying tunnel through which the zone of each of said eye rods loaded with solution or suspension is passed.

6. An eye rod, for administering an active substance to the eye, comprising a rod-like member having on the outer surface thereof a dry coating of said active substance, said coating of active substance being confined to a band extending from a point proximate to, but not including, one end of said rod-like member.

7. A process for loading an eye rod with an active substance, said process comprising the steps of:
 (a) applying a predetermined number of droplets of a predetermined volume of a solution or suspension of said active substance to an intended zone of said eye rod,
 (b) simultaneously or subsequently rotating said eye rod about its longitudinal axis, in order to uniformly distribute said solution or suspension on the surface of said eye rod in said zone, and
 (c) then removing the solvent or suspension agent by evaporation in order to leave dried active substance on said eye rod.

8. A device for loadng eye rods with active substance, said device comprising:
 (a) means for conveying a plurality of eye rods along a motion path in a spaced-apart, substantially parallel relationship;
 (b) means located at a point along said motion path for applying a predetermined number of droplets of a predetermined volume of a solution or suspension of active substance to an intended zone of each eye rod conveyed past said point on said motion path;
 (c) means for rotating each eye rod being conveyed along said motion path about its longitudinal axis, in order to uniformly distribute the solution or suspension of active substance applied to said eye rod on the surface thereof in said intended zone; and,
 (c) means for evaporating the solvent or suspension agent from the charge of active substance which has been applied to each eye rod, as said eye rod moves along said motion path, in order to leave dried active substance on said eye rod.

9. The device of claim 8 wherein said means for conveying said eye rods along said motion path comprises a first conveyor belt driven in a first direction at a first speed and wherein said means for rotating said eye rods comprises a second conveyor belt driven in a second direction opposite to that of the first and at a second speed which is less than that of the first, said second belt being in a spaced-apart, parallel relationship to said first belt, the distance between said two belts being such that eye rods placed upon said first belt are contact by said second belt.

10. The device of claim 9 further comprising an endless roller chain which is conveyed along said motion path and which has spaces between transverse links thereof adapted to receive eye rods therein, said roller chain serving to maintain said eye rods in a spaced-apart, substantially parallel relationship.

11. The device of claim 8 wherein said means for conveying said eye rods comprises a conveyor wheel having notches or recesses on its outer surface for receiving eye rods and means for rotatingly driving said wheel in a first direction and wherein said means for rotating said eye rods comprises a belt, driven in a direction opposite to that of said first direction, which contacts eye rods being conveyed by said conveyor wheel.

* * * * *